United States Patent [19]

Tozzolino

[11] 4,088,781
[45] May 9, 1978

[54] SULPHONIUM COMPOUNDS AND THEIR APPLICATION

[75] Inventor: Pierre Tozzolino, Bizanos, France

[73] Assignee: Societe Nationale Elf Aquitaine (Prod.), Courbevoie, France

[21] Appl. No.: 702,582

[22] Filed: Jul. 6, 1976

[30] Foreign Application Priority Data

Jul. 11, 1975 France .................. 75 21826

[51] Int. Cl.$^2$ ............... A61K 31/255; C07C 141/04
[52] U.S. Cl. ................................ 424/303; 424/335; 260/459 R; 260/607 B
[58] Field of Search ......... 260/459 R, 607 B, 458 R; 424/303, 335

[56] References Cited

U.S. PATENT DOCUMENTS

| 2,121,823 | 6/1938 | Piggott | 260/459 R |
| 2,204,976 | 6/1940 | Peski et al. | 260/458 R |
| 2,335,119 | 11/1943 | Hoeffelman | 260/458 R |
| 3,639,492 | 2/1972 | Campbell | 260/655 |
| 3,652,255 | 3/1972 | Osieka | 71/76 |

FOREIGN PATENT DOCUMENTS 2,208,894  8/1973  Germany .................. 260/458 R

*Primary Examiner*—Nicky Chan
*Attorney, Agent, or Firm*—Ostrolenk, Faber, Gerg & Soffen

[57] ABSTRACT

New chemical products formed by sulphates of alkyl and sulphonium, the latter having on its sulphur atom an alkyl containing 1 to 6 carbon atoms, a second alkyl containing at least 6 carbon atoms, and a 2-hydroxyethyl group.

These products are prepared by reacting a dialkyl sulphate with a sulphide of an alkyl containing at least 6 carbon atoms and of —CH$_2$CH$_2$OH.

The sulphonium compounds of this type, and particularly the compound in which the heavy alkyl is a n-octyl, are useful as fungicides.

8 Claims, No Drawings

SULPHONIUM COMPOUNDS AND THEIR APPLICATION

This invention relates to a new group of organic sulphonium compounds; it also covers the preparation of these compounds and their application.

Various organic products containing the sulphonium group have been known for many years. For example, U.K. pat. specification No. 464,330 in 1937 disclosed sulphonium metho-sulphates in which the S atom bears radicals such as methyl, cetyl, dodecyl, tetradecyl, octadecyl, benzyl, phenyl, tolyl, and so on. These products were proposed as disinfectants, bacteriocides, and fungicides, but since their activity was not completely satisfactory, attempts were subsequently made to modify them in various ways, by introducing more active groups into their molecule, e.g. nitrophenols (U.S. Pat. No. 2,366,176), chlorophenols (U.S. Pat. No. 2,402,016), dienes (U.S. Pat. No. 3,494,965), amino-groups (U.S. Pat. No. 3,478,154), hydroxy groups (German laid-open Specification No. 2,130,775) and others (U.K. pat. Specification No. 1,228,094).

The applications of these different sulphonium compounds in combating plant parasites are limited because of their phytotoxicity.

This invention relates to new sulphonium compounds which in addition to their advantageous surface-active properties have a fungicidal activity which can be utilized without harm to plants.

The new products according to the invention are double sulphates of alkyls and sulphonium whose sulphur atom bears an alkyl having 1 to 6 carbon atoms, preferably a lower alkyl having 1 to 4 carbon atoms, a heavy alkyl having at least 6 carbon atoms, and a 2-hydroxy-ethyl group. These compounds therefore correspond to the formula:

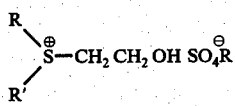

where R may be methyl, ethyl, propyl, isopropyl, butyl, isobutyl or tert-butyl, R' being an alkyl containing at least 6 carbon atoms and, more particularly, an alkyl having 6 to 18 carbon atoms.

A compound according to the invention of great industrial value is 2-hydroxyethyl methyl octyl sulphonium metho-sulphate, i.e. the substance of the above formula wherein R is a methyl and R' an octyl. This product may also be called 2-hydroxyethyl-methyl-octyl sulphonium and methyl sulphate.

This new chemical product is in the form of a very viscous liquid at ordinary temperature. At 260° C and at a pressure of about 0.1 mm Hg, it decomposes without having distilled. Its refractive index is:
$n_D^{20} = 1.4795$
$n_D^{30} = 1.4808$ As indicated above, the new sulphoniums according to the invention are very useful as fungicides and suitable for protecting plants against numerous types of cryptogamic attack. From this aspect, the R' octyl compound is quite remarkable: its fungicidal activity is greater than that of its other homologues, while given suitable dosage it causes no harm to plants. From this aspect, its application is a marked advance over the various sulphonium-based fungicides proposed hitherto.

The invention also relates to a very practical process for the preparation of the above-described new products. Although this process is based on a general principle of producing the sulphonium compounds more particularly from the corresponding sulphides, it is characterized in that the organic sulphide used contains the 2-hydroxyethyl group. The new process therefore comprises reacting an alkyl 2-thio-ethanol with dialkyl sulphate. Since the reaction is exothermic, the temperature of the medium is controlled so that it remains between approximately 50° and 100° C. The resulting sulphonium is purified by means of a suitable solvent, e.g. ethyl ether or isopropyl ether, which eliminates the residual initial organic sulphide and the dialkyl sulphate.

The invention is illustrated by the following Examples without any limiting force.

EXAMPLE 1

Preparation of 2-hydroxy-ethyl-methyl-octyl sulphonium metho-sulphate 126 g (1 mole) of methyl sulphate $(CH_3)_2SO_4$ is added dropwise to 190 g of 2-hydroxy-ethyl and n-octyl sulphide $CH_3(CH_2)_7$—$SCH_2CH_2OH$ (1 mole), at ordinary temperature with agitation and the reaction medium being cooled so as to prevent the temperature rising above 80° C. This temperature is maintained for 1 hour after the addition of the sulphate, which also takes 1 hour. After this total time of 2 hours, the medium is cooled to ordinary temperature and then washed with ether until complete disappearance of the initial sulphide and methyl sulphate. This elimination is followed by gas chromatography and thin-layer chromatography.

The sulphonium metho-sulphate

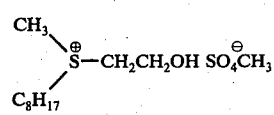

is obtained in the form of a viscous product with a 90% yield. Its refractive index $n_D^{20}$ is 1.4795.

EXAMPLE 2

Preparation of 2-hydroxy-ethyl-heptyl-methyl sulphonium metho-sulphate

The process of Example 1 was repeated using n-heptyl and 2-hydroxy-ethyl sulphide as the initial sulphide, i.e. $CH_3(CH_2)_6$—$SCH_2CH_2OH$. The sulphonium, in which R' is a heptyl, was obtained with an 85% yield in this way.

EXAMPLE 3

Preparation of 2-hydroxy-ethyl-methyl-dodecyl sulphonium metho-sulphate

The procedure was the same as in the preceeding examples using 1 mole of 2-hydroxy-ethyl-dodecyl sulphide $C_{12}H_{25}SCH_2CH_2OH$ with 1 mole of dimethyl sulphate.

The sulphonium $C_{12}H_{25}S^{\oplus}(CH_3)CH_2CH_2OH\ CH_3SO_4^{\ominus}$ was obtained with a 92% yield. The product is solid and crystallizes in acetone. The melting point is of 92° C.

EXAMPLE 4

Preparation of 2-hydroxy-ethyl-methyl-tetradecyl sulphonium metho-sulphate

The procedure was the same as in the preceeding Examples using 1 mole of 2-hydroxy-ethyl-tetradecyl sulphide $C_{14}H_{29}$—S—$CH_2CH_2OH$ with 1 mole of dimethyl sulphate. The corresponding sulphonium was obtained with an 85% yield, was free from methyl sulphate and sulphide and melted at 95° C. This product can be recrystallized from acetone.

EXAMPLE 5

Tests on in vivo fungicidal activity of 2-hydroxy-ethyl-methyl-octyl sulphonium metho-sulphate Suspensions of this product in different concentrations were prepared in aqueous acetone and 125 ppm of wetting agent ("Tween 20") were added. The suspension was applied to the leaves of young plants having one or two leaves completely developed. The controls used were identical leaves of the same plant treated with an aqueous acetone suspension containing the surfactant alone. 24 hours after this treatment, the treated leaves were inoculated with spores of the fungus under study; the samples were then left for 24 hours in a water-vapour-saturated atmosphere, and then for 10 or 14 days at 18° C, the air having a relative humidity of 80–90%. The development of the disease on the leaves was then examined: the percentage of reduction of the fungus growth is given below in comparison with that of the non-treated controls.

| Cucumber-Powdery mildew (ERYSIPE CICHORACEARUM fungus) | |
|---|---|
| After 14 days | Percentage reduction of disease |
| 2,000 ppm of sulphonium | 82 |
| 500 ppm of sulphonium | 83 |
| 125 ppm of sulphonium | 69 |
| 125 ppm of surfactant alone | <5 |
| Barley - Powdery mildew (ERYSIPE GRAMINIS fungus) | |
| After 10 days | Percentage reduction of disease |
| 500 ppm of sulphonium | 91 |
| 125 ppm of sulphonium | 83 |
| 31 ppm of sulphonium | 69 |
| surfactant alone | <5 |
| Peas - PHASEOLUS VULGARIS - Blight (UROMYCES PHASEOLI Fungus) | |

With a concentration of 2,000 ppm of sulphonium, the development of the disease after 14 days was reduced by 50% whereas the reduction was less than 5% with the control suspension.

These results show that a concentration of 500 ppm (w/v) is sufficient to check the development of mildew on cucumber or on a grass by more than 80%. The 50% reduction of pea blight by using 2 000 ppm is still very good, since the conventional fungicides, e.g. mancozeb or maneb, must be used in concentrations of about 250 g/hl, i.e. 2 500 ppm, for the same application.

EXAMPLES 6 to 14

A number of sulphonium compounds according to the invention having the general structure

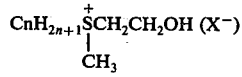

were tested in various concentrations against Erysipe cichoracearum, in the manner described in Example 4 in connection with cucumber mildew.

The percentage reduction of fungus growth are given in the following Table.

| Example N° | Value of n | Nature of X⁻ | Growth reduction with: | | |
|---|---|---|---|---|---|
| | | | 2000 ppm | 500 ppm | 125 ppm |
| 6 | 7 | $CH_3SO_4$ | 80 % | 15 % | 0 |
| 7 | 8 | $CH_3SO_4$ | 84 % | 80 % | 70 % |
| 8 | 9 | $CH_3SO_4$ | | 81 % | 48 % |
| 9 | 10 | $CH_3SO_4$ | | 86 % | 42 % |
| 10 | 12 | $CH_3SO_4$ | | 37 % | |
| 11 | 12 | I | XX | XX | XX |
| 12 | 14 | I | XX | XX | 10 |
| 13 | 16 | $CH_3SO_4$ | XX | XX | 5 |
| 14 | 16 | I | XX | 35$^x$ | 10 |

These tests show the exceptional activity of the sulphonium where n = 8, 9, 10 (Examples 7, 8, 9) and particularly the sulfonium with n = 8. For n = 12 - 16, (Examples 11-14) high phytotoxicity was found as denoted by XX, and this prevented the efficacy of the product from being evaluated.

The sulphonium iodide with $C_{16}$ (Example 14) has a more moderate phytotoxicity (X) in the case of 500 ppm.

EXAMPLES 15 to 25

Several sulphonium compounds according to the invention, having the general structure

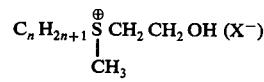

have been tested at various concentrations, against Uromyces phaseoli, to combate bean rust, and against Puccinia recondita which caused brown wheat rust.

The following results have been obtained

| Example n° | Value of n | nature of X⁻ | Against Uromyces phaseoli Growth reduction % with | |
|---|---|---|---|---|
| | | | 500 ppm | 125 ppm |
| 15 | 9 | $CH_3SO_4$ | 76 | 42 |
| 16 | 9 | $SO_4H$ | 86 | |
| 17 | 10 | $CH_3SO_4$ | 70 | 0 |
| 18 | 10 | $SO_4H$ | 73 | 18 |
| 19 | 12 | $CH_3SO_4$ | 73 | 18 |
| 20 | 12 | $SO_4H$ | 77 | 26 |
| | | | Against Puccinia recondita | |
| 21 | 9 | $SO_4H$ | 62 | — |
| 22 | 10 | $CH_3SO_4$ | 59 | — |
| 23 | 10 | $SO_4H$ | 75 | — |
| 24 | 12 | $CH_3SO_4$ | 80 | — |
| 25 | 12 | $SO_4H$ | 75 | 84 |

These results show that the above compounds have a good antirust activity.

EXAMPLE 26

Some tests, made in the condition of preceding examples, show that the compound containing 12 carbon atoms has also an activity against the Phytophthora infestans which causes potato-blight. 75 to 80% of growth reduction are obtained with a concentration of 2,000 ppm.

I claim:

1. A dialkyl 2-hydroxyethyl sulfonium metho-sulfate having fungicidal properties of the formula

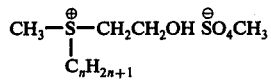

wherein $n$ is 8, 9 or 10.

2. Methyl octyl 2-hydroxyethyl sulfonium metho-sulfate according to claim 1.

3. Methyl nonyl 2-hydroxyethyl sulfonium metho-sulfate according to claim 1.

4. Methyl decyl 2-hydroxyethyl sulfonium metho-sulfate according to claim 1.

5. An aqueous suspension comprising 30–2,000 ppm of the dialkyl 2-hydroxyethyl sulfonium metho-sulfate of claim 1.

6. The aqueous suspension of claim 5 wherein said sulfonium metho-sulfate is methyl octyl 2-hydroxyethyl sulfonium metho-sulfate.

7. The aqueous suspension of claim 6 wherein said sulfonium metho-sulfate is methyl nonyl 2-hydroxyethyl sulfonium metho-sulfate.

8. The aqueous suspension of claim 7 wherein said sulfonium metho-sulfate is methyl decyl 2-hydroxyethyl sulfonium metho-sulfate.

UNITED STATES PATENT AND TRADEMARK OFFICE
CERTIFICATE OF CORRECTION

PATENT NO. : 4,088,781
DATED : May 9, 1978
INVENTOR(S) : Pierre Tozzolino

It is certified that error appears in the above-identified patent and that said Letters Patent are hereby corrected as shown below:

For the assignee read -- SOCIETE NATIONALE ELF-AQUITAINE (PRODUCTION) --

In column 1, at line 10 and at lines 22-23, delete "Specification".

Column 2, line 66 for

"$C_{12}H_{25}S^{\oplus}(CH_3)CH_2CH_2OH \quad CH_3SO_4^{B}$" read

-- $C_{12}H_{25}S^{\oplus}(CH_3)CH_2CH_2OH \quad CH_3SO_4^{\ominus}$ --.

Signed and Sealed this

Twenty-sixth Day of December 1978

[SEAL]

Attest:

RUTH C. MASON
Attesting Officer

DONALD W. BANNER
Commissioner of Patents and Trademarks